United States Patent [19]

Carchidi

[11] Patent Number: 4,976,617
[45] Date of Patent: Dec. 11, 1990

[54] DENTAL IMPLANT SCREW DRIVER SYSTEM

[76] Inventor: Joseph E. Carchidi, 98 Westwood Dr., Whitman, Mass. 02382

[21] Appl. No.: 345,667

[22] Filed: May 1, 1989

[51] Int. Cl.⁵ ............................................. A61C 3/00
[52] U.S. Cl. ................................... 433/141; 433/159
[58] Field of Search ................... 433/4, 141, 159, 174, 433/221, 225

[56] References Cited

U.S. PATENT DOCUMENTS

| | | | |
|---|---|---|---|
| 1,743,910 | 1/1930 | Boatner | 433/226 |
| 2,504,227 | 4/1950 | Rubba | 433/159 |
| 3,376,643 | 4/1968 | Nealon | 433/215 |
| 3,834,026 | 9/1974 | Klein | 433/159 |
| 3,898,738 | 8/1975 | Linder | 433/159 |
| 4,177,562 | 12/1979 | Miller et al. | 433/174 |
| 4,189,839 | 2/1980 | Manuel | 433/4 |
| 4,490,116 | 12/1984 | Deutsch et al. | 433/225 |

Primary Examiner—John J. Wilson
Assistant Examiner—Michael Lynch
Attorney, Agent, or Firm—John A. Haug

[57] ABSTRACT

A screw driver system particularly adapted for use in placement and removal of dental implant screws is shown to comprise a forceps holder having distal pincer portions adapted to firmly engage the head of a screw driver at an optimal angle to permit improved visibility of the work area and access thereto when the system is placed in the mouth of a patient.

11 Claims, 3 Drawing Sheets

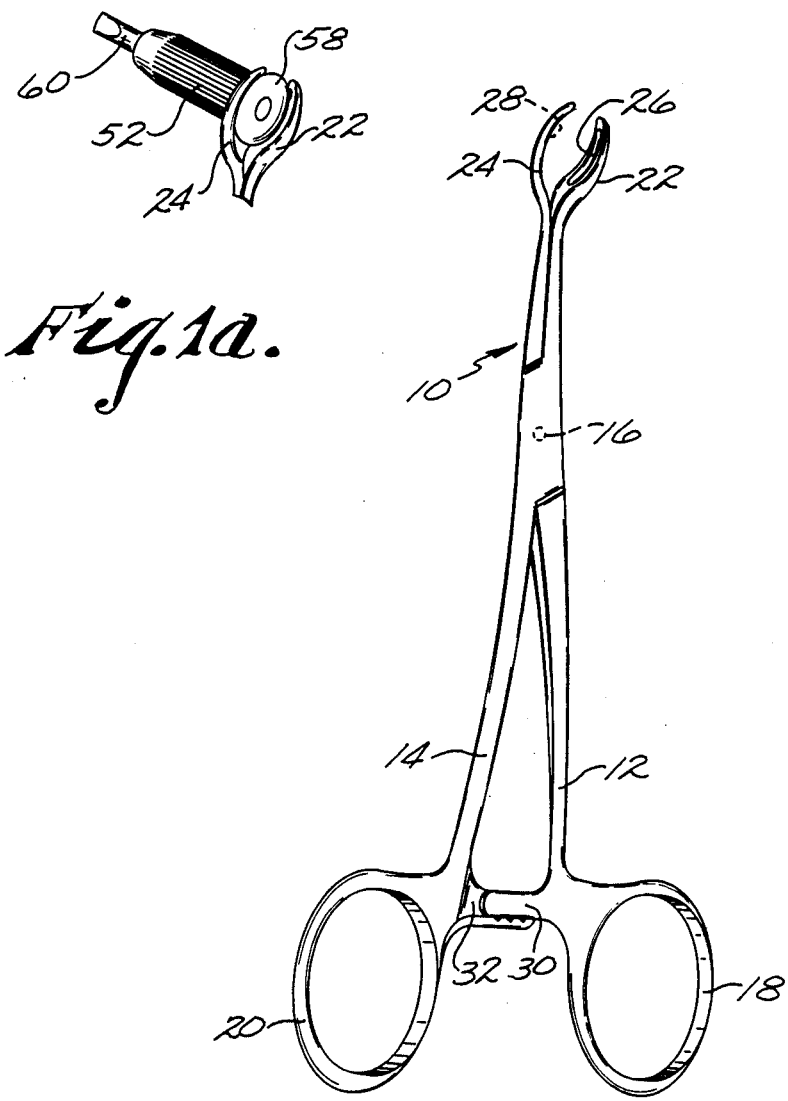
Fig.1a.
Fig.1.
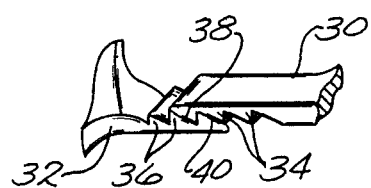
Fig.2.

DENTAL IMPLANT SCREW DRIVER SYSTEM

FIELD OF INVENTION

This invention relates generally to dental implants and more particularly to a screw driver system for use with dental implants.

BACKGROUND OF INVENTION

Placement and removal of healing and fixation screws for dental implants has been carried on by dental practitioners for many years and typically involves the use of the fingers of one hand to position a screw driver in the recess of a patient's mouth with the fingers of the other hand used to rotate the screwdriver. Due to the very limited space and accessibility available, particularly when the situs is in the back of the mouth cavity, the procedure is awkward and cumbersome. The problem is further exacerbated by the limitation of visibility caused by the requirement of both hands being in the work area.

It is an object of the present invention to provide a screw driver system which overcomes the above noted limitations. It is yet another object to provide a screw driver system for use with dental implants which permits improved control and visibility of the installation and removal of healing and fixation screws.

Other objects and advantages of the present invention will become more fully apparent from the following detailed description when read in conjunction with the accompanying drawings.

SUMMARY OF THE INVENTION

Briefly, a screw driver system made in accordance with the invention comprises a forceps holder having first and second elongated elements hingedly interconnected intermediate their ends with first and second pincers formed at the distal free end portion of one end of the elements. The pincers are movable between open, unlocked and closed locked positions with a screwdriver receivable between the pincers and firmly grasped therebetween when the pincers are in the closed, locked position so that a force can be applied along the longitudinal axis of the screwdriver from a point laterally removed therefrom.

According to a feature of a preferred embodiment of the invention a groove is formed in each pincer and is adapted to receive a peripheral portion of the head or attachment portion of the screw driver. The head portion of the screw driver is selected to have a diameter slightly larger than the distance between the grooves when the pincers are in the closed, locked position resulting in a strong bias gripping the head through the spring characteristic of the elongated elements.

According to another feature of the invention the pincers lie in a plane which intersects the plane in which the remainder of the elongated elements lie by an angle preferably between approximately 30°–45° to enable better accessibility to the work area.

According to yet another feature of the invention the locking mechanism comprises a finger extending from each elongated element with a set of teeth formed on each finger with the teeth adapted to intermesh upon closing of the elements.

A second embodiment includes pincers that are adapted to completely circumscribe a reduced diameter portion of a modified screw driver to hold the screw driver.

BRIEF DESCRIPTION OF DRAWINGS

FIG. 1 is a perspective view of the forceps holder made in accordance with the invention;

FIG. 1a is a perspective view of the pincers portion of the forceps holder shown with a screw driver held by the pincers;

FIG. 2 is an enlarged broken away portion showing intermeshed teeth of the locking mechanism of FIG. 1;

DESCRIPTION OF PREFERRED EMBODIMENTS

Figure 3:
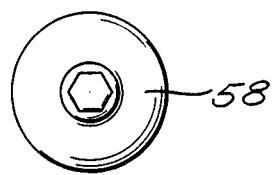
FIGS. 3–5 are top, front and bottom views respectively of the screw driver shown in FIG. 1a but shown enlarged for purposes of clarity of illustration.

Turning now to the drawings, forceps screw driver holder 10 shown in FIG. 1 comprises first and second elongated elements 12, 14 hingedly connected intermediate their ends at 16 and being formed of stainless steel or other suitable material having good spring characteristics. Elements 12, 14 have conventional finger loop portions 18, 20 at a first end and crescent shaped pincer portion 22, 24 at a second end thereof.

Crescent shaped portions 22, 24 having their concave shaped portions facing one another are each provided with an elongated depressed area, grooves 26, 28 respectively with the entire crescent portion preferably lying in a plane at an angle of approximately 30° relative to the plane in which the remainder lies, although the angle could be between approximately 30° and 45° and still be effective. As shown in FIG. 1, the distal free ends of the pincer portions 22, 24 are shown slightly spaced from one another.

A locking mechanism is formed on the elongated elements adjacent the loop portion 18, 20 in the form of respective fingers 30, 32 each having a set 34, 36 respectively of outwardly extending teeth facing one another, each tooth being generally in the configuration of a right triangle in profile and so adapted that urging of the loop portions 18, 20 toward one another will cause the inclined plane portion 38 on tooth 34 closer to the free distal end of finger 30 to ride up the inclined plane portion 40 of tooth 36 closer to the free distal end of finger 32 until the outer teeth snap over the knife edge defining the outer teeth. Continued movement of the loop portions toward one another will eventually cause the entire set of teeth on the two fingers to intermesh thereby firmly locking elements 12, 14 in a fixed position.

Once locked, elements 12, 14 can be separated by urging one loop portion out of the plane of the other loop portion.

Figure 4:
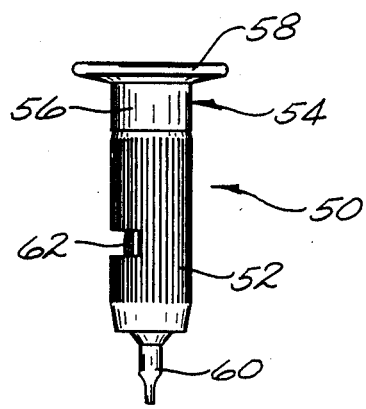
Figure 5:
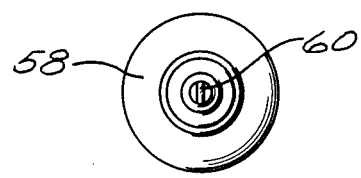

As seen in FIGS. 3–5 a screw driver 50 is shown slightly enlarged relative to holder 10 in FIG. 1a. Screw driver 50 has a body portion 52 having a head 54 rotatably mounted thereon, the head having a shank portion 56 and a flange 58 projecting outwardly from portion 56. Screw driver 50 is provided with a suitable blade portion 60 which, if desired, can be replaceable to provide different size or configuration tools, i.e., tools other than of the straight blade type. In any event, portion 60 is locked in body 52 at 62 as by epoxy or other suitable conventional locking means.

Grooves 26, 28 of pincers 22, 24 are adapted to receive the outer periphery of flange 58. The outer diameter of flange 58 is slightly larger than the distance between the bottom surface of the grooves 26, 28 when in the locked position so that when the locking mechanism is engaged with the flange 58 of the screw driver received in the grooves the inherent spring characteristics of the elongated elements, serve to firmly hold the screw driver by the pincers. The screw driver can be held in one hand via the forceps holder in a selected location, for example, within the interior portion of the mouth cavity, with suitable force exerted on the screw driver along the longitudinal axis of the screw driver, either upwardly or downwardly, through the forceps holder from a point removed from the longitudinal axis of the screw driver. Further, the hand grasping the screw driver can be placed out of the field of vision due to the angle between the elongated elements and the pincers. The body and blade portion of the screw driver can then conveniently be rotated by the fingers of the other hand while still being able to see the work area. It will be noted that the screw driver can extend from either side of the forceps holder to provide an acute as well as an obtuse angle for optimum flexibility for the practitioner depending upon the particular procedure being performed.

Figure 6:
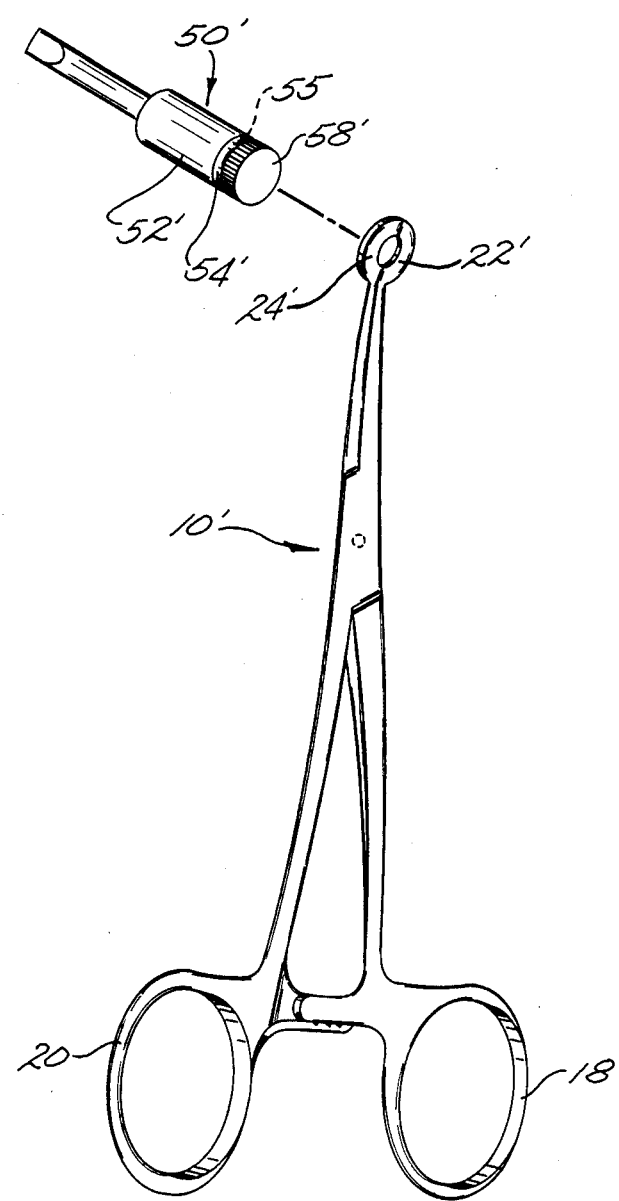
FIG. 6 is a perspective view of a second embodiment of the invention showing a modified forceps holder and screw driver.

An alternative embodiment of the invention is shown in FIG. 6 which shows pincers 22', 24' formed to essentially completely circumscribe a reduced diameter attachment portion 54' of screw driver 50'. In this embodiment when loops 18, 20 are separated from one another pincers 22', 24' are placed around shaft portion 55 between head portion 58' and body portion 52' so that a vertical force can be exerted on screw driver 50' through forceps holder 10', through pincers 22', 24' exerted on body portion 52'.

While there has been illustrated and described what at present is considered to be the preferred embodiments of the present invention it will be understood by those skilled in the art that various changes and modifications may be made and equivalents may be substituted for elements thereof without departing from the true scope of the invention. It is intended that the invention will include all embodiments falling within the scope of the appended claims.

What is claimed is:

1. A screw driver system comprising a forceps holder having engagement means to engage a screw driver attachment portion, the engagement means having first and second pincers each formed with an elongated groove movable between open, unlocked and closed, locked positions, a locking mechanism to lock the pincers in the closed, locked position, a screw driver having a blade portion and an attachment portion and having a longitudinal axis extending therethrough, the screw driver attachment portion having a head portion rotatably attached to the screw driver, the head portion having an outwardly extending circular flange removably received in the grooves and securely clasped by the pincers when in the closed, locked position, the attachment portion of the screw driver removably received in the pincers so that a force can be applied to the screw driver blade along its longitudinal axis from a point laterally removed from the blade portion of the screw driver.

2. A system according to claim 1 in which the pincers comprise first and second elongated elements hingedly connected to one another intermediate their ends, the elements lying in a first plane and in which the pincers are inclined relative to the elements and extend out of the plane in which the elements lie, the pincers lying in a second plane which intersects the first plane.

3. A system according to claim 2 in which the angle between the planes is approximately 30°.

4. A system according to claim 2 in which the angle between the planes is between approximately 30° and 45°.

5. A system according to claim 1 in which the pincers comprise first and second elongated elements hingedly connected to one another intermediate their ends, the locking mechanism comprising a finger extending from each elongated element in alignment with and toward each other, a set of teeth formed on each finger, the set on one finger facing the set on the other finger and adapted to intermesh upon selected movement of the elements toward one another.

6. A system according to claim 5 in which the teeth are generally triangular in profile having a ramp portion to facilitate closing motion and a snap over knife edge to obtain secure locking.

7. A screw driver system comprising a forceps holder having engagement means to engage a screw driver attachment portion, the engagement means having first and second pincers movable between open, unlocked and closed, locked positions, a locking mechanism to lock the pincers in the closed, locked position, the screw driver having a blade portion and an attachment portion and having a longitudinal axis extending therethrough, the attachment portion of the screw driver removably received in the pincers so that a force can be applied to the screw driver blade along its longitudinal axis from a point laterally removed from the blade portion of the screw driver, the attachment portion of the screw driver having a reduced diameter portion intermediate its end and the pincers are each generally semi-circular forming a circular opening when closed which is slightly larger than the reduced diameter portion.

8. A screw driver system comprising a first member formed of first and second elongated elements having first and second ends and being hingedly connected together intermediate their ends, engagement means to engage a screw driver attachment head portion, the engagement means having generally crescent shaped pincer portions having inwardly disposed concave portions formed at one end of each element, the concave portion of the crescent shaped pincer portions facing one another, an elongated groove formed in each concave portion, a locking mechanism formed on the elements to lock the elements with the pincer portions in a fixed selection position, a second member comprising a screw driver having a body portion, a tool portion fixedly attached to the body portion and an attachment head portion rotatably connected to the body portion, the attachment head portion having a circular flange the periphery of which is removably received in the grooves of the pincers to securely mount the screw driver in the holder when the elements are in the closed, locked position.

9. A screw driver system according to claim 8 in which the first and second elements lie in a first plane and the pincer portions extend out of the plane in which the elements lie, the pincers lying in a second plane intersected by the first plane.

10. A screwdriver system according to claim 9 in which the angle between the planes is approximately 30°.

11. A screwdriver system according to claim 9 in which the angle between the planes is between approximately 30° and 45°.

* * * * *